(12) United States Patent
Bernard-King et al.

(10) Patent No.: US 6,316,488 B1
(45) Date of Patent: Nov. 13, 2001

(54) ANTIBIOTIC COMPOUND

(75) Inventors: Aurora M. Bernard-King, Asbury; Michael J. Salvatore, Jr., South Plainfield; Athanasios Tsipouras, Edison; Kennth E. Wilson, Westfield, all of NJ (US)

(73) Assignee: Merck & Co., Inc., Rahway, NJ (US)

(*) Notice: Subject to any disclaimer, the term of this patent is extended or adjusted under 35 U.S.C. 154(b) by 0 days.

(21) Appl. No.: 09/589,028

(22) Filed: Jun. 7, 2000

Related U.S. Application Data

(60) Provisional application No. 60/139,911, filed on Jun. 17, 1999.
(51) Int. Cl.$^7$ .................. A61K 31/40; C07D 207/20; C12N 1/20
(52) U.S. Cl. .............................. 514/423; 548/537
(58) Field of Search ................ 548/537; 514/423

(56) References Cited

U.S. PATENT DOCUMENTS

| | | | |
|---|---|---|---|
| 5,510,369 | * | 4/1996 | Lumma et al. ............ 514/422 |
| 5,744,487 | * | 4/1998 | Ohshima et al. .......... 514/326 |
| 6,239,150 | * | 5/2001 | Oshima et al. ........... 514/330 |

FOREIGN PATENT DOCUMENTS

| | | |
|---|---|---|
| 0 007 614 B1 | 2/1980 | (EP) . |
| 0 072 014 B1 | 2/1983 | (EP) . |

OTHER PUBLICATIONS

J. Biol. Chem. 1984, 259(1), 383–385.*

* cited by examiner

*Primary Examiner*—Floyd D. Higel
*Assistant Examiner*—Kamal Saeed
(74) *Attorney, Agent, or Firm*—Soonhee Jang; Mark R. Daniel; Sylvia A. Ayler

(57) ABSTRACT

Fermentation of a nutrient medium with a eubacterium pseudomonas sp. Yieds a novel broad spectrum antibiotic compound of structure I

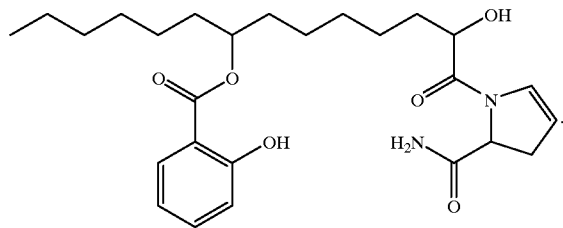

3 Claims, 2 Drawing Sheets

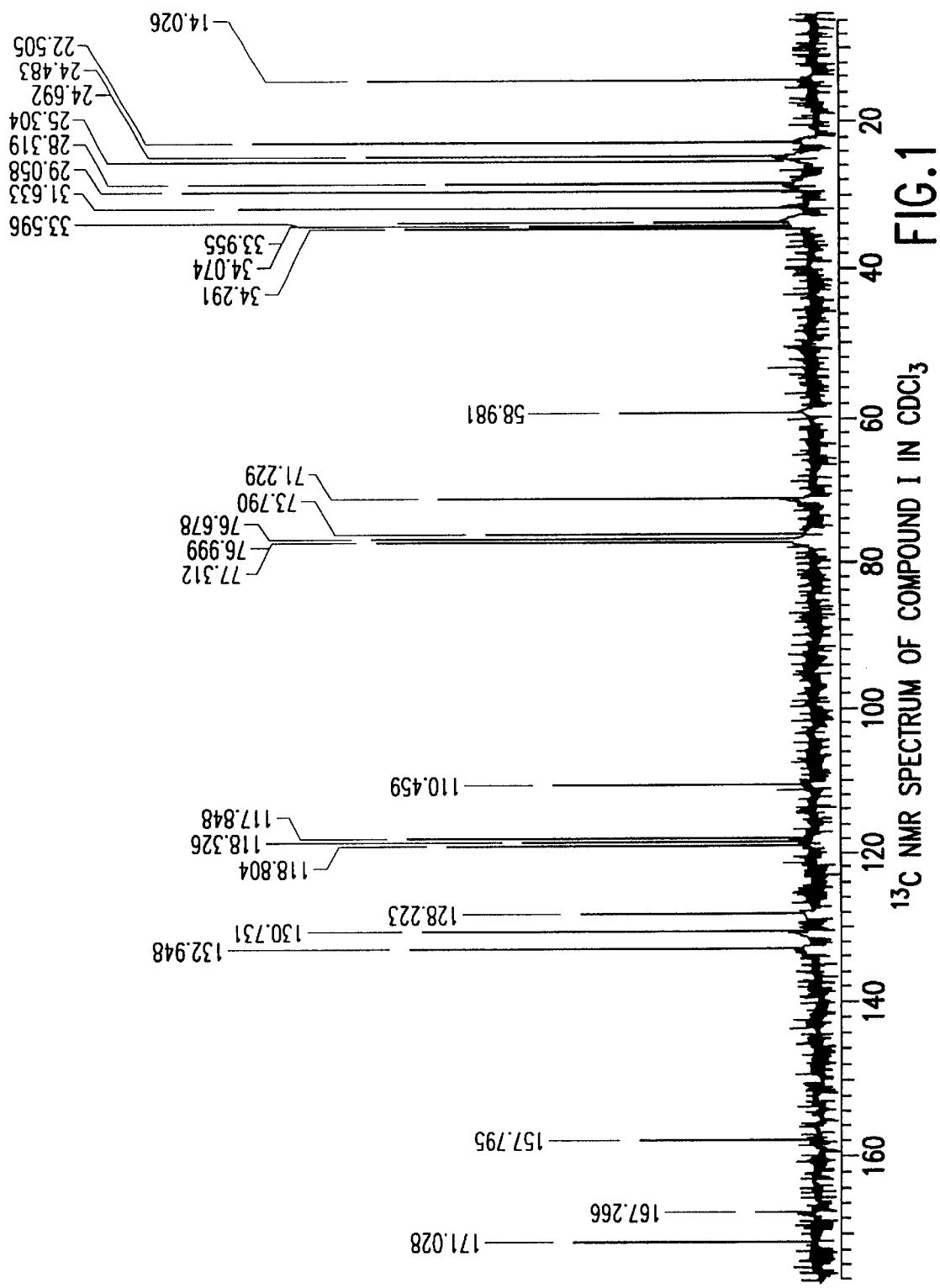

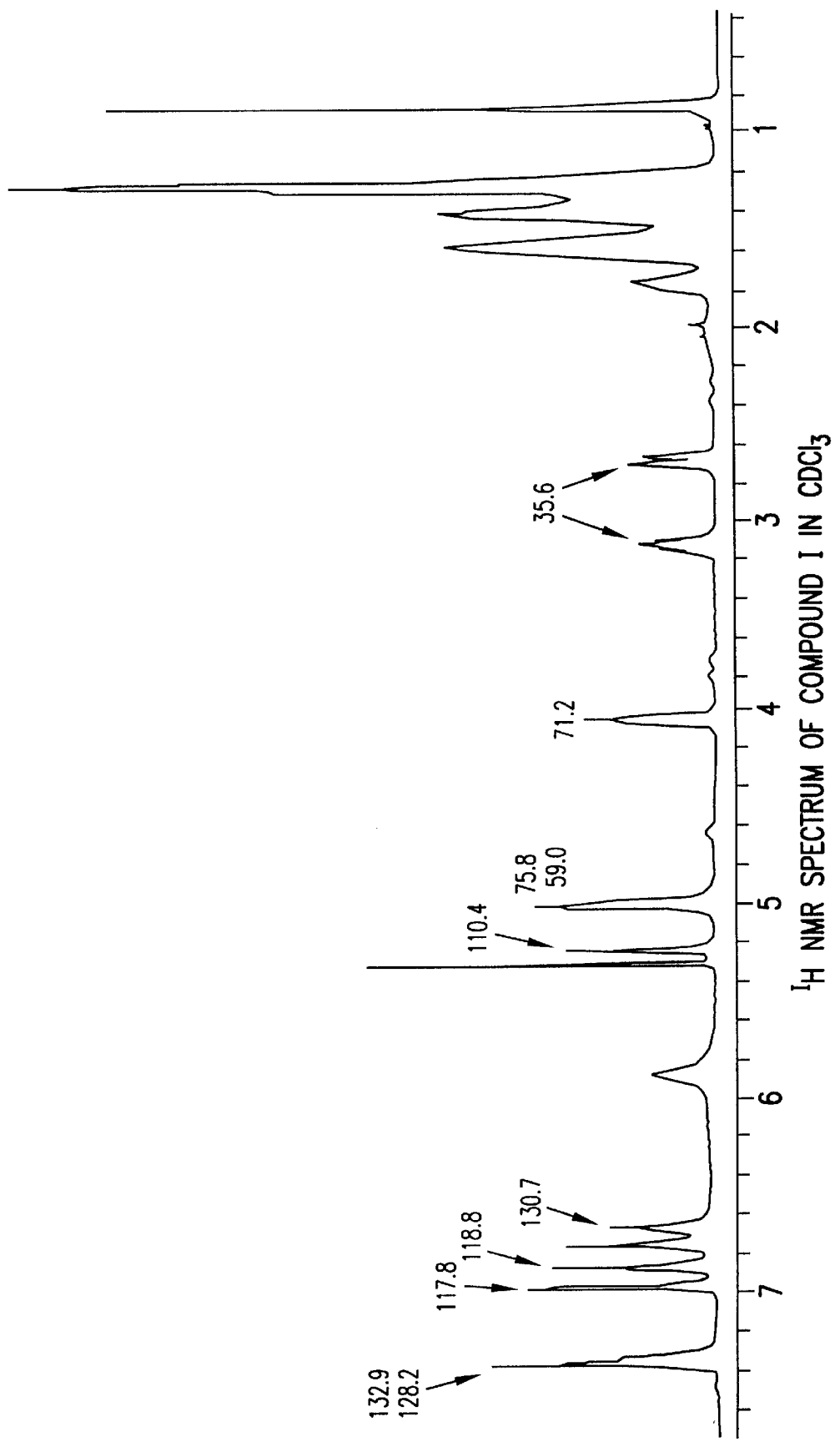
FIG.2 $^1H$ NMR SPECTRUM OF COMPOUND I IN $CDCl_3$

ANTIBIOTIC COMPOUND

This application claims the benefit of U.S. Provisional Application No. 60/139,911, filed Jun. 17, 1999.

BACKGROUND OF THE INVENTION

The present invention relates to a broad spectrum aralkyl-peptide antibiotic compound that is useful in treating gram negative and gram positive bacterial infections.

Infections caused by gram negative bacteria are a growing medical concern as many of these bacteria are resistant to various gram negative antibiotics, especially antibiotics for treating *Pseudomonas aeruginosa, Vibrio cholerae, Vibrio parahemolyticus, Actinobacter calcoaeticus* and *Stenotrophomonas maltophilia*. In addition, many Gram positive bacteria are resistant to these Gram negative antibiotics, especially *Staphylococcus aureus, Staphylococcus hemolyticus,* Pediococcus spp., and *Streptococcus pyogenes* and *Streptococcus pneumoniae*. The antibiotic of this invention, thus comprises an important contribution to therapy for treating infections which are resistant to various known antibiotics.

A prior art compound that is also an aralkyl-peptide and which is used for treating bacterial infections is Vibriobactin, which has the following structure:

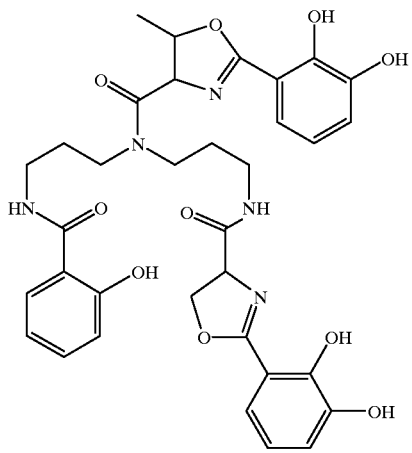

In the present invention, the aralkyl-peptide antibiotic is produced from a eubacterial fermentation and possesses antibacterial activity against gram negative and gram positive bacterial infections many of which have demonstrated resistance to currently available antibiotics.

SUMMARY OF THE INVENTION

This invention is concerned with a novel aralkyl-peptide antibiotic of the formula I:

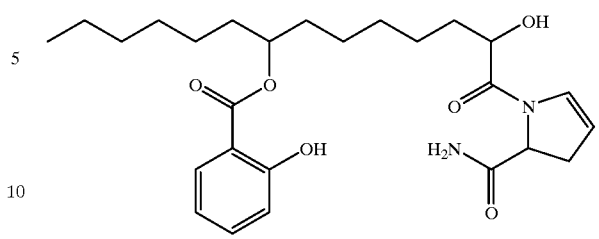

or a pharmaceutically acceptable salt thereof which is effective in the treatment of gram negative and gram positive bacterial infections.

The invention is also concerned with a process for the production of Compound I by fermentation with a eubacterial Pseudomonas sp.

The invention is also concerned with a process for isolating Compound I from the fermentation broth.

BRIEF DESCRIPTION OF THE DRAWINGS

FIG. 1 is a $^{13}$C NMR spectrum of Compound I in $CDCl_3$.

FIG. 2 is a $^1$H NMR spectrum of Compound 1 in $CDCl_3$.

DETAILED DESCRIPTION OF THE INVENTION

This invention is concerned with Compound I of structural formula:

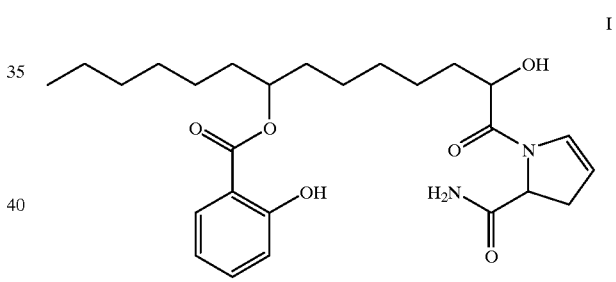

or a pharmaceutically acceptable salt thereof.

The pharmaceutically acceptable salts of the compound of this invention include the conventional non-toxic salts as formed, from non-toxic inorganic or organic bases. For example, such conventional non-toxic salts include those derived from inorganic bases such as an alkali or alkaline earth metal hydroxide, e.g., potassium, sodium, lithium, calcium, or magnesium, and the like: and the salts prepared from organic bases such as an amine, e.g., dibenzylethylenediamine, trimethylamine, piperidine, pyrrolidine, benzylamine and the like, or a quaternary ammonium hydroxide such as tetramethylammonium hydroxide and the like.

The pharmaceutically acceptable salts can be synthesized from the compounds of this invention by conventional chemical methods. Generally, the salts are prepared by reacting the free acid with stoichiometric amounts or with an excess of the desired salt-forming inorganic or organic base in a suitable solvent or various combinations of solvents.

Compound I of this invention is a broad spectrum antibiotic useful in the treatment of gram negative and gram positive bacterial infections. It demonstrates antibacterial activity primarily against *Pseudomonas aeruginosa* species which are resistant to many known antibiotics. The minimum inhibitory concentration (MIC) values for these test strains range from 0.12 to 64 ug/mL. In addition, the Gram negative test strains *Vibrio cholerae* and *Vibrio parahemolyticus* (MIC values of 32 to 128 ug/mL), *Acinetobacter calcoaceticus* (MIC values of 32 to 128 ug/mL) and *Stenotrophomonas maltophilia* (MIC value of 64 g/mL) were susceptible. Also, the Gram positive test strains *Staphylococuus aureus* and *Staphylococuus hemolyticus* (MIC values of 32 to 64 ug/ml), Pediococcus spp. (MIC values of 32 ug/mL), *Streptococcus pyogenes* and *Streptococcus pneumoniae* (MIC valuesof 32 ug/mL) were also susceptible.

The compound of the invention can be formulated in pharmaceutical compositions by combining the compound with a pharmaceutically acceptable carrier. Examples of such carriers are set forth below.

The compound may be employed in powder or crystalline form, in liquid solution, or in suspension. It may be administered by a variety of means; those of principal interest include: topically, orally and parenterally by injection (intravenously or intramuscularly).

Compositions for injection, one route of delivery, may be prepared in unit dosage form in ampules, or in multidose containers. The injectable compositions may take such forms as suspensions, solutions, or emulsions in oily or aqueous vehicles, and may contain various formulating agents. Alternatively, the active ingredient may be in powder (lyophillized or non-lyophillized) form for reconstitution at the time of delivery with a suitable vehicle, such as sterile water. In injectable compositions, the carrier is typically comprised of sterile water, saline or another injectable liquid, e.g., peanut oil for intramuscular injections. Also, various buffering agents, preservatives and the like can be included.

Topical applications may be formulated in carriers such as hydrophobic or hydrophilic bases to form ointments, creams, lotions, in aqueous, oleaginous or alcoholic liquids to form paints or in dry diluents to form powders.

Oral compositions may take such forms as tablets, capsules, oral suspensions and oral solutions. The oral compositions may utilize carriers such as conventional formulating agents, and may include sustained release properties as well as rapid delivery forms.

The dosage to be administered depends to a large extent upon the condition and size of the subject being treated, the route and frequency of administration, the sensitivity of the pathogen to the Compound, the virulence of the infection and other factors. Such matters, however, are left to the routine discretion of the physician according to principles of treatment well known in the antibacterial arts.

The compositions for administration to humans per unit dosage, whether liquid or solid, may contain from about 0.01% to as high as about 99% of Compound I, one embodiment of the range being from about 10–60%. The composition will generally contain from about 15 mg to about 2.5 g of Compound I, one embodiment of this range being from about 250 mg to 1000 mg. In parenteral administration, the unit dosage will typically include pure Compound I in sterile water solution or in the form of a soluble powder intended for solution, which can be adjusted to neutral pH and isotonicity.

The invention described herein also includes a method of treating a bacterial infection in a mammal in need of such treatment comprising the administration of Compound I to the mammal in an amount effective to treat the infection.

One embodiment of the methods of administration of Compound I includes oral and parenteral methods, e.g., i.v. infusion, i.v. bolus and i.m. injection.

For adults, about 5–50 mg of Compound I per kg of body weight given one to four times daily is preferred. The preferred dosage is 250 mg to 1000 mg of the antibacterial given one to four times per day. More specifically, for mild infections a dose of about 250 mg two or three times daily is recommended. For moderate infections against highly susceptible gram positive organisms a dose of about 500 mg three or four times daily is recommended. For severe, life-threatening infections against organisms at the upper limits of sensitivity to the antibiotic, a dose of about 1000–2000 mg three to four times daily may be recommended.

For children, a dose of about 5–25 mg/kg of body weight given 2, 3, or 4 times per day is preferred; a dose of 10 mg/kg is typically recommended.

Compound I is an antibacterial agent active against *Pseudomonas aeruginosa* isolates resistant to various antibiotics. Many antibacterial agents are susceptible to attack by a renal enzyme known as dehydropeptidase (DHP). This attack or degradation may reduce the efficacy of the antibacterial agent. The compound of the present invention, on the other hand, is less subject to such attack, and therefore may not require the use of a DHP inhibitor. However, such use is optional and contemplated to be part of the present invention. Inhibitors of DHP and their use with carbapenems are disclosed in, e.g., [European Patent Application Nos. 79102616.4, filed Jul. 24, 1979 (Patent No. 0 007 614); and 82107174.3, filed Aug. 9, 1982 (Publication No. 0 072 014)].

Compound I of the present invention may, where DHP inhibition is desired or necessary, be combined or used with the appropriate DHP inhibitor as described in the aforesaid patents and published application. The cited European Patent Applications define the procedure for determining DHP susceptibility of the present carbapenem and disclose suitable inhibitors, combination compositions and methods of treatment. A preferred weight ratio of Compound I: DHP inhibitor in the combination compositions is about 1:1.

A preferred DHP inhibitor is 7-(L-2-amino-2-carboxyethylthio)-2-(2,2-dimethylcyclopropanecarboxamide)-2-heptenoic acid or a useful salt thereof.

Another aspect of this invention is the process for producing Compound I which comprises cultivating a Pseudomonas sp. microorganism in a suitable nutrient medium and then recovering the compound of this invention from the fermentation broth. The organism in question was identified as the eubacterium, Pseudomonas sp. following taxonomic studies. It was deposited in the Merck Culture Collection on Jun. 23, 1998 and assigned accession number MB 5731. It was subsequently placed on permanent deposit with the American Type Culture Collection (ATCC), 12301 Parklawn Drive, Rockville, Md., 20852 and has been assigned accession number PTA-183. Any restrictions relating to public access to the microorganism shall be irrevocably removed upon patent issuance. Although the use of this particular species is described in connection with this invention, there may be other species and mutants of the above organism capable of producing Compound I, and their use is contemplated in carrying out the process of this invention.

The compound of structural formula I is produced by the aerobic fermentation of a suitable medium under controlled conditions via inoculation with a culture of the eubacterium, Pseudomonas sp. (ATCC accession number.PTA-183). The suitable medium is preferably aqueous and contains sources of assimilable carbon, nitrogen, and inorganic salts.

The medium employed for fermentation by the Pseudomonas sp. is primarily the well-known Difco Tryptic Soy Broth, either alone or with added nutrients commonly used by those skilled in the art.

It should be noted that the nutrient media described herein are merely illustrative of the wide variety of media which may be employed and are not intended to limit the scope of this invention in any way.

The fermentation is conducted at temperatures ranging from about 10° C. to about 40° C.; however for optimum results it is preferred to conduct the fermentation at about 28° C. The pH of the nutrient medium during the fermentation can be about 5.5 to about 7.5.

It is to be understood that for the fermentative production of the compound of this invention, the invention is not limited to the use of the particular Pseudomonas sp. with ATCC accession number PTA-183. It is especially desired and intended that there be included in the scope of this invention the use of other natural or artificial mutants produced or derived from the described cultures, or other variants or species of the Pseudomonas genus insofar as they can produce the compound of this invention. The artificial production of mutant species or strains of Pseudomonas from PTA-138 may be achieved by conventional, physical or chemical mutagens, for example, ultraviolet irradiation of the described culture, or nitrosoguanidine treatment and the like. Recombinant DNA techniques such as protoplast fusion, plasmid incorporation, chromosome fragment incorporation and the like also may prove useful.

EXAMPLE 1

Step 1 Fermentation

Fermentation of the culture was performed by aseptically transferring a volume of 0.1 ml of thawed frozen vegetative cell suspension to 50 ml of production medium in a 250 ml baffled Erlenmeyer flask. The production medium, contained glycerol (50 g) and Tryptic Soy Broth (Difco) (30 g) in 1 liter of deionized water. Cultures in production medium were incubated at 28° C. and shaken at 220 rpm for 3 days.

Step 2 Isolation

To a 1.7 liter regrowth of eubacterial culture (pH 6.5), 1.7 L acetone was added and the mixture was stirred for 1 hour. The extracted solids were collected by centrifugation and discarded. The centrifugate was saturated with NaCl and the pH adjusted to 4.5 (4N HCl). Ethyl acetate (1.7 L) was added and the mixture left overnight at 4° C. The organic layer was separated from the aqueous layer and evaporated to give 1.9 g of residue.

1.8 g of the residue was taken up in ethyl acetate, loaded onto a silica column (250 g) and washed with 3 column volumes each of a 50:50 v:v ethyl acetate-hexane (fraction 1); 25:75 MeOH-ethyl acetate v:v (fraction 2) and 100% MeOH (fraction 3). Activity of interest was in fraction 2, which was evaporated to give 0.5 g of an oily residue.

12 mg of essentially pure compound of formula I was obtained by preparative HPLC of the oily residue (55% acetonitrile-water, 0.1% TFA, semipreparative DuPont Zorbax RX C-8; 8 mil/min flow rate, 3 injections) followed by concentration and lyophilization.

Step 3: Physiochemical Properties of I

The structure of Compound I was dermined by the use of mass spectroscopy, $^1$H NMR and $^{13}$C NMR.

Molecular Weight: 474

Molecular Formula $C_{30}H_{42}N_2O_8$ $^{13}$C NMR (CDCl$_3$) δ(ppm): 177.3; 171.3; 161.2; 157.2; 134.5; 127.9; 123.0; 118.9; 116.8; 88.7; 75.6; 71.0; 58.2; 34.5; 33.8; 33.7; 31.7; 30.8; 29.1; 27.6; 26.2; 25.4; 24.5; 24.1; 22.6; 14.1. See FIG. 1.

$^1$H NMR (CDCl$_3$) δ(ppm): 7.37(m, 1H); 7.34 (d, 1H); 6.97 (t, 1H); 6.87 (br. S, 1H); 6.67 (br. S, 1H); 5.24 (br. S, 1H); 5.00 (m, 2H); 4.0 (m, 1H); 3.1 (br, t, 1H); 2.7 (br. D, 1H); 1.2–1.6 methylene envelope, 0.9 (t, 3H. See FIG. 2.

What is claimed is:

1. A compound of structural formula I:

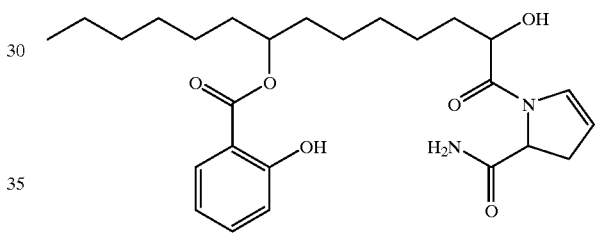

or a pharmaceutically acceptable salt thereof.

2. A pharmaceutical composition comprising a pharmaceutically acceptable carrier and an effective amount of a compound of structure I.

3. A method of treating a bacterial infection in a host in need of such treatment comprising the administration of an effective amount of the compound of formula I.

* * * * *